(12) United States Patent
Senetar

(10) Patent No.: US 6,872,867 B1
(45) Date of Patent: Mar. 29, 2005

(54) START-UP OF A METHANOL-TO-OLEFIN PROCESS

(75) Inventor: John J. Senetar, Naperville, IL (US)

(73) Assignee: UOP LLC, Des Plaines, IL (US)

( * ) Notice: Subject to any disclaimer, the term of this patent is extended or adjusted under 35 U.S.C. 154(b) by 66 days.

(21) Appl. No.: 10/621,788

(22) Filed: Jul. 17, 2003

(51) Int. Cl.[7] .............................................. C07C 1/207
(52) U.S. Cl. ...................... 585/951; 585/638; 585/639; 585/640
(58) Field of Search ................................ 585/951, 638, 585/639, 640

(56) References Cited

U.S. PATENT DOCUMENTS

| | | | |
|---|---|---|---|
| 4,387,263 A | 6/1983 | Vogt et al. | 585/640 |
| 4,587,373 A | 5/1986 | Hsia | 585/639 |
| 5,095,163 A | 3/1992 | Barger | 585/640 |
| 5,126,308 A | 6/1992 | Barger et al. | 502/214 |
| 5,191,141 A | 3/1993 | Barger et al. | 585/640 |
| 6,166,282 A | 12/2000 | Miller | 585/638 |
| 6,403,854 B1 | 6/2002 | Miller et al. | 585/638 |

Primary Examiner—Thuan D. Dang
(74) Attorney, Agent, or Firm—John G. Tolomei; Mark Goldberg

(57) ABSTRACT

A catalytic conversion process using a fluidized conversion zone, which requires a minimum superficial gas velocity to function properly, and a motor-driven, capacity-limited product compressor zone is started up using a thermal compressor by establishing two start-up gas recirculation circuits, one using the product compression zone running at high pressure to recirculate about 40 to 60 vol-% of the effluent gas stream from the conversion zone and the other running at low pressure and carrying the remaining portion of the effluent gas stream from the fluidized conversion zone where the high pressure circuit supplies motive gas to the thermal compression zone and the low pressure circuit supplies suction gas to the thermal compressor and the resulting compressed discharge gas enables the catalytic process to start up without the use of a dedicated motor-driven start-up compressor.

19 Claims, 2 Drawing Sheets

US 6,872,867 B1

START-UP OF A METHANOL-TO-OLEFIN PROCESS

FIELD OF INVENTION

The present invention specifically relates to the start-up of a methanol-to-olefin (MTO) process utilizing a fluidized MTO conversion zone with a product compression zone that is sized to handle only about 20 to 60% of the volume of the effluent gas stream removed from the MTO conversion zone due to presence therein of significant amounts of an easily condensable substance, steam, where a novel two recycle gas stream flow configuration is used in conjunction with a thermal compressing zone and the product compression zone in order to provide a recycle gas stream which has sufficient velocity to enable the proper operation of the solid/gas cyclone separating means utilized in the fluidized MTO conversion zone. A successful start-up is thereby enabled without the use of a dedicated motor-driven start-up compressor. The present invention relates more generally to the use of a thermal compressor in a start-up method for any catalytic conversion process that uses a fluidized reaction zone and that has an undersized product compression zone where the method enables effective cyclone operation in the fluidized reaction zone associated therewith.

BACKGROUND OF THE INVENTION

A major portion of the worldwide petrochemical industry is concerned with the production of light olefin materials and their subsequent use in the production of numerous important chemical products via polymerization, oligomerization, alkylation and the like well-known chemical reactions. Light olefins include ethylene, propylene and mixtures thereof. These light olefins are essential building blocks for the modern petrochemical and chemical industries. The major source for this materials in present day refining is the steam cracking of petroleum feeds. For various reasons including geographical, economic, political and diminished supply considerations, the art has long sought a source other than petroleum for the massive quantities of raw materials that are needed to supply the demand for these light olefin materials. In other words, the holy grail of the R & D personnel assigned to work in this area is to find a way to effectively and selectively use alternative feedstocks for this light olefin production application thereby lessening dependence of the petrochemical industry on petroleum feedstocks. A great deal of the prior art's attention has been focused on the possibility of using hydrocarbon oxygenates and more specifically methanol as a prime source of the necessary alternative feedstock. Oxygenates are particularly attractive because they can be produced from such widely available materials as coal, natural gas, recycled plastics, various carbon waste streams from industry and various products and by-products from the agricultural industry. The art of making methanol from these types of raw materials is well established and typically involves the use of one or more of the following procedures: (1) manufacture of synthesis gas by any of the known techniques typically using a nickel or cobalt catalyst followed by the well-known methanol synthesis step using relatively high pressure with a copper-based catalyst; (2) selective fermentation of various organic agricultural products and by-products in order to produce oxygenates; or (3) various combinations of these techniques.

Given the established and well-known technologies for producing oxygenates from alternative non-petroleum raw materials, the art has focused on different procedures for catalytically converting oxygenates such as methanol into the desired light olefin products. These light olefin products that are produced from non-petroleum based raw materials must of course be available in quantities and purities such that they are interchangeable in downstream processing with the materials that are presently produced using petroleum sources. Although many oxygenates have been discussed in the prior art, the principal focus of the two major routes to produce these desired light olefins has been on methanol conversion technology primarily because of the availability of commercially proven methanol synthesis technology. A review of the prior art has revealed essentially two major techniques that are discussed for conversion of methanol to light olefins. The first of these MTO processes is based on early German and American work with a catalytically conversion zone containing a zeolitic type of catalyst system. Representative of the early German work is U.S. Pat. No. 4,387,263 which was filed in May of 1982 in the U.S. without a claim for German priority. This '263 patent reports on a series of experiments with methanol conversion techniques using a ZSM-5-type of catalyst system wherein the problem of DME recycle is a major focus of the technology disclosed. Although good yields of ethylene and propylene were reported in this '263 patent, they unfortunately were accompanied by substantial formation of higher aliphatic and aromatic hydrocarbons which the patentees speculated might be useful as an engine fuel and specifically as a gasoline-type of material. In order to limit the amount of this heavier material that is produced, the patentees of the '263 patent propose to limit conversion to less than 80% of the methanol charged to the MTO conversion step. This operation at lower conversion levels necessitated a critical assessment of means for recovering and recycling not only unreacted methanol but also substantial amounts of a DME intermediate product. The focus then of the '263 patent invention was therefore on a DME and methanol scrubbing step utilizing a water solvent in order to efficiently and effectively recapture the light olefin value of the unreacted methanol and of the intermediate reactant DME.

This early MTO work with a zeolitic catalyst system was then followed up by the Mobil Oil Company who also investigated the use of a zeolitic catalyst system like ZSM-5 for purposes of making light olefins. U.S. Pat. No. 4,587,373 is representative of Mobil's early work and it acknowledged and distinguished the German contribution to this zeolitic catalyst based MTO route to light olefins. The inventor of the '373 patent made two significant contributions to this zeolitic MTO route the first of which involved recognition that a commercial plant would have to operate at pressure substantially above the preferred range that the German workers in this field had suggested in order to make the commercial equipment of reasonable size when commercial mass flow rates are desired. The '373 patent recognized that as you move to higher pressure for the zeolitic MTO route in order to control the size of the equipment needed for commercial plant there is a substantial additional loss of DME that was not considered in the German work. This additional loss is caused by dissolution of substantial quantities of DME in the heavy hydrocarbon oil by-product recovered from the liquid hydrocarbon stream withdrawn from the primary separator. The other significant contribution of the '373 patent is manifest from inspection of the flow scheme presented in FIG. 2 which prominently features a portion of the methanol feed being diverted to the DME absorption zone in order to take advantage of the fact that there exist a high affinity between methanol and DME thereby downsizing the size of the scrubbing zone required relative to the scrubbing zone utilizing plain water that was suggested by the earlier German work.

Primarily because of an inability of this zeolitic MTO route to control the amounts of undesired $C_4^+$ hydrocarbon products produced by the ZSM-5 type of catalyst system, the art soon developed a second MTO conversion technology based on the use of a non-zeolitic molecular sieve catalytic material. This branch of the MTO art is perhaps best illustrated by reference to UOP's extensive work in this area as reported in numerous patents of which U.S. Pat. No. 5,095,163, U.S. Pat. No. 5,126,308 and U.S. Pat. No. 5,191,141 are representative. This second approach to MTO conversion technology was primarily based on using a catalyst system comprising a silicoaluminophosphate molecular sieve (SAPO) with a strong preference for a SAPO species that is known as SAPO-34. This SAPO-34 material was found to have a very high selectivity for light olefins with a methanol feedstock and consequently very low selectivity's for the undesired corresponding light paraffins and the heavier materials. This SAPO catalyzed MTO approach is known to have at least the following advantages relative to the zeolitic catalyst route to light olefins: (1) greater yields of light olefins at equal quantities of methanol converted; (2) capability of direct recovery of polymer grade ethylene and propylene without the necessity of the use of extraordinary physical separation steps to separate ethylene and propylene from their corresponding paraffin analogs; (3) sharply limited production of by-products such as stabilized gasoline; (4) flexibility to adjust the product ethylene-to-propylene weight ratios over the range of 1.5:1 to 0.75:1 by minimal adjustment of the MTO conversion conditions; and (5) significantly less coke make in the MTO conversion zone relative to that is experienced with the zeolitic catalyst system.

Despite the promising developments associated with the SAPO-catalyzed route to light olefins, there are still substantial hurdles to overcome before an economically attractive SAPO-catalyzed MTO process can be fully realized. One very substantial economic problem is associated with the start-up of such an MTO process. One unusual feature of an MTO process is the very large amount of steam that is present in the effluent from the MTO conversion zone. The stoichiometry of the MTO reaction is such that for every mole of methanol charged to the MTO conversion zone at least one mole of water is co-produced and furthermore if water is present in the feed (i.e. crude methanol is charged) or steam is used as a diluent in order to lower the partial pressure of methanol in the reaction zone there can be large amounts of additional steam in the effluent from the MTO reaction zone. The amount of steam in a typical MTO reactor effluent stream is about 40 to 80% of the volume of the effluent stream depending somewhat on the exit temperature and pressure of this effluent stream as well as the degree of conversion and the extent of the use of a water diluent and water contamination of the feed. The operation of a successful MTO process is thus forced to deal with the presence of large amounts of readily condensable material in the effluent gas stream from the MTO conversion zone. This situation necessitates the use of a rather large quench zone on the effluent stream along with associated heat exchange procedures as is explained in my patent U.S. Pat. No. 6,403,854 in order to eliminate substantially all of this water contaminant from this effluent stream to produce a hydrocarbon-rich portion of this effluent stream for further downstream processing. As is explained in some detail in the discussion of FIG. 4 of my '854 patent, a preferred MTO flow scheme employs a product compression zone on this hydrocarbon-rich portion of the effluent gas stream that is recovered from the overhead of the quench zone. Due to the dramatic volume shrinkage that occurs across the quench zone when the water by-product of the MTO reaction is cooled and condensed and due somewhat to the sharp drop in temperature that occurs when the effluent gas stream traverses the quench zone and the associated heat exchangers, the product compression zone operates on an input gas stream which is only about 20 to 60 vol-% of the effluent gas volume originally withdrawn from the MTO conversion zone. Since the product compression zone is sized on the basis of the volume of gas stream that it is expected to handle during on-stream operation, this shrinkage phenomenon that is inherent in the operation of an MTO process is very advantageous when specifying this size of the mechanical compressing means that are used in the compression zone in order to achieve the desired downstream processing pressure. Since the economics of acceptable commercial practice for compression of the hydrocarbon portion of the effluent stream from a commercial scale fluidized MTO unit require the use of one or more variable speed centrifugal compressors that have a limited capacity to handle volumes of gas beyond their design capacity, the opportunity to use the product compression zone as the chief motive force for driving a start-up gas through the fluidized MTO conversion zone appears at first blush to be limited. In other words, it is clear from the discussion above that the process design engineer who attempts to design a start-up protocol for an MTO process using a fluidized conversion zone and to rely on the product compression zone for start-up gas circulation faces a monumental task.

For various reasons well-articulated in UOP's patents U.S. Pat. No. 6,403,854 and U.S. Pat. No. 6,166,282 (all of the teachings of which are hereby specifically incorporated by reference), the consensus of the art relating to the design of an MTO process points to the use of a fluidized reaction zone as the preferred commercial solution to the problem of efficiently and effectively using a SAPO type catalyst system in this type of service. Given this fluidization constraint on the type of reaction system, there is an additional design parameter that must be considered in formulating a start-up protocol for an MTO process using a fluidized MTO conversion zone. Not unexpectedly this design parameter is associated with the catalyst separation technology that is required for proper operation of a fluidized reaction zone. Standard industry practice for fluidized catalyst separation from product gas is shown in the sole drawing of the '854 patent (attached hereto as FIG. 2) and involves the use of one or more cyclones in a disengagement zone typically located above the reaction zone and frequently coupled with a riser termination device that gives an initial gas/solid separation. When an expensive catalyst system such as a SAPO-34 based catalyst system is used (i.e. the SAPO-34 catalyst system is expected to be at least an order of magnitude higher in cost then standard high performance FCC catalyst), it is essential to the economics of the process that catalyst losses be minimized especially during sharp transitions associated with start-up and shutdown of the MTO conversion zone. It is extremely important in other words that the cyclones in the fluidized reaction zone function properly during start-up in order to avoid significant catalyst losses due to excessive attrition induced by start-up turbulence and catalyst blow out caused by operating cyclones at less then there minimum specified superficial gas velocity. Established cyclone design standards require a superficial linear velocity in the inlet throat of the cyclone of about 10.7 to 16.8 m/sec (35 to 50 ft/sec) for proper operation of the cyclone and this requirement is an additional design constraint on the start-up protocol for MTO process using a fluidized MTO conversion zone.

The problem addressed by the present invention is then to design a start-up method for a catalytic MTO process that uses a fluidized MTO conversion zone containing one or more cyclones to separate reaction products from catalyst where the method meets or exceeds the required cyclone minimum superficial linear velocity for initiating catalyst circulation and uses the undersized (i.e. for start-up purposes) motor-driven product compression zone to drive the start-up gas stream through the fluidized MTO conversion zone without employing a large and expensive motor-driven dedicated start-up compressor for start-up gas circulation.

SUMMARY OF THE INVENTION

The primary object of the present invention is to provide a start-up method for an MTO process using a fluidized MTO conversion zone employing one or more cyclones for catalyst separation where the method meets the minimum gas velocity circulation requirements for these cyclones, uses the product compression zone to supply motive force for start-up gas circulation and does not require the use of an expensive dedicated start-up compressor. A secondary object is to provide such a start-up method and avoid the capital cost and operating and maintenance expense associated with a large dedicated start-up motor-driven compressor that is only used on an infrequent basis. A more general objective is to provide a start-up method, that does not require a dedicated start-up compressor, for a catalytic conversion process that use a fluidized conversion zone to produce an effluent stream containing a significant amount of one or more readily condensable substances and therefore has an undersized product compression zone for start-up gas circulation purposes.

I have now found a start-up method for an MTO process using a fluidized MTO conversion zone that solves the problem defined above by using two start-up gas recycle streams, one operated at a low pressure [typically about 138 to 310 kPa (20 to 45 psi)] and the other at a high pressure [typically about 1931 to 2758 kPa (280 to 400 psi)] in conjunction with a thermal compression zone and a start-up gas heater where the heated high pressure start-up gas recycle stream provides the motive gas to the thermal compression zone (which is not a machine since it has no moving parts) and the low pressure stream provides the suction gas to this thermal compression zone, thereby enabling the discharge gas from the compression zone (i.e. a blend of the heated high pressure recycle stream and the compressed low pressure recycle stream) to enter the fluidized reaction zone at a velocity which quickly builds to a level which satisfies the minimum requirement for cyclone operation and enables safe catalyst circulation in the fluidization zone and the introduction of methanol feed.

Another finding is that the instant start-up method can be used to start-up any catalytic process that uses a fluidized reaction zone containing one or more cyclones and that has an undersized (i.e. for purposes of start-up) product compression zone due to presence in the effluent gas stream of a significant amount of one or more readily condensable substance. The use of a thermal compressor and two recycle gas streams enables the start-up of such a catalytic process without the use of a dedicated, motor-driven start-up compression. Specific examples of the scope of use for this broader aspect of the present invention are catalytic processes: 1) for the production of light olefins from oxygenate such as alcohols other then methanol, ethers, aldehydes, ketones and the like, from sulfides such as mercaptans and from amines such as methylamine; 2) for the production of olefins using stream dehydrogenation where steam is used in large amounts to lower the partial pressure of the hydrocarbon reactant; 3) for the production of olefinic materials using stream cracking of hydrocarbons and 4) any other process that uses a readily condensable diluent or makes a significant amount of one or more readily condensable products and/or by-product and as a result has an undersized product compression zone for start-up purposes.

In one embodiment consequently, the present invention is a method of start-up of a catalytic MTO process comprising a fluidized MTO reaction zone containing cyclones requiring a minimum superficial gas velocity in order to function properly, an effluent quench zone, a motor-driven product compression zone that is sized to handle only 20 to 60% of the volume of the reaction zone effluent stream at design capacity and a light olefin and oxygenate recovery zone where the start-up is conducted without the use of an additional motor-driven start-up compressor and with the use of a thermal compression zone having a motive gas inlet, a suction gas inlet and a discharge gas outlet. The first step of the start-up method involves charging the MTO reaction zone with an inert start-up gas in amount sufficient to provide an effluent gas stream that can be recirculated through the fluidized MTO reaction zone until it is replaced by the methanol feed stream. The second step involves passing a first portion of the resulting effluent gas stream into the product compression zone and compressing it therein to provide a high-pressure recycle start-up gas stream. The next step involves heating at least a first portion of this high pressure gas stream and charging the resulting heated stream to the motive gas inlet of the thermal compression zone to produce a discharge gas stream and recycling the resulting discharge gas stream from the thermal compression zone back to the MTO reaction zone thereby establishing a first start-up gas circuit. A second portion of the start-up gas effluent stream is passed directly from the MTO reaction zone to the suction gas inlet of the thermal compression zone and therein increased in pressure and admixed with the high pressure recycle gas to form the discharge gas stream which is returned to the MTO conversion zone thereby establishing a second start-up gas circuit. The temperature of the heated high pressure gas stream is then increased until the temperature of the MTO reaction zone reaches at least about 300° to 400° C. (572° to 752° F.). The pressure of the discharge gas stream is also increased until the pressure differential across the MTO reaction zone is sufficient to drive the discharge gas there through at a velocity which meets or exceeds the minimum cyclone superficial gas velocity. When the specified temperatures and pressures are achieved the next step involves circulating catalyst particles in the MTO reaction zone using the discharge gas stream from the thermal compression zone as the fluidizing gas. Once catalyst circulation is established in the MTO conversion zone and the cyclones are functioning properly, the introduction of methanol feed to this conversion zone is started along with the start of contacting the effluent gas stream with a quenching medium in the quench zone in order to condense any steam contained therein. A second portion of the high-pressure gas stream recovered from the product compression zone is then diverted into the light olefin and oxygenate recovery zone and operation of this zone is initiated. The last step then involves increasing the rate of flow of the methanol feed into the MTO reaction zone until it reaches the desired operating level while simultaneously decreasing the amount of the first portion of the high pressure gas stream recovered from the product compression zone that is passed into the first start-up gas circuit until the desired flow rate of methanol feed into the MTO reaction zone is established and the thermal compression zone is blocked off.

A second embodiment involves the start-up method as described above where high pressure stream is injected into the motive gas inlet of the thermal compression zone in admixture with the high pressure gas recycle stream once the temperature of the MTO conversion zone and any catalyst contained therein reaches a level of 300° to 400° C. (572° to 752° F.) thereby avoiding any condensation of water in the pores of the catalyst particles.

A broader embodiment of the start-up method of the present invention involves a method of starting-up any catalytic process comprising a fluidized reactor zone containing one or more cyclones requiring a minimum superficial gas velocity in order to function properly and a motor-driven product compression zone that is sized to handle only about 20 to 60 vol-% of the reaction zone effluent gas stream at design capacity and that cannot by itself during start-up provide the required superficial gas velocity for the one or more cyclones in the fluidized reaction zone. The start-up of this catalytic process is conducted without the use of an additional motor-driven start-up compressor and with the use of a thermal compressor having a motive gas inlet, a suction gas inlet, and a discharge gas outlet. The first step of the start-up method involves charging the reaction zone with an inert start-up gas in an amount sufficient to provide an effluent gas stream for recirculation. A first portion of the resulting effluent gas stream in the next step is passed to the product compression zone and compressed therein to provide a high pressure gas stream. The third step involves heating at least a first portion of the high pressure gas stream, charging the resulting heated high pressure gas stream to the motive gas inlet of the thermal compressor to produce a discharge gas stream arid recycling the resulting discharge gas stream from the thermal compressor back to the reaction zone thereby establishing a first start-up gas circuit. A second portion of the effluent gas stream is then passed directly to the suction gas inlet of the thermal compressor, wherein it is compressed using energy contained in the motive gas and the resulting compressed gas is passed into admixture with the discharge gas stream thereby establishing a second start-up gas circuit. The next step involves increasing the temperature of the circulating heated high pressured gas stream until the temperature of the reaction zone and any catalyst contained therein reaches at least about 300° to 400° C. (572° to 752° F.) and increasing the pressure of the discharge gas stream until the pressure differential across the reaction zone is sufficient to drive the discharge gas stream there through at a velocity which meets or exceeds the minimum cyclone superficial gas velocity. Circulation of catalyst particles in the reactor zone is then started using the discharge gas stream from the thermal compressor as the fluidizing gas and charging of a minor amount of feed to the reaction zone is begun while a commensurate second portion of the high pressure gas stream recovered from the product compression zone is passed into a product recovery zone. In the last step, the amount of the feed passed into the reaction zone is increased while simultaneously decreasing the amount of the first portion of the high pressure gas stream passed into the first start-up gas circuit until the desired flow rate of the feed into the reaction zone is established and the thermal compression zone is blocked off.

Another embodiment involves the start-up method described in any of these embodiments wherein the inert start-up gas is selected from the group consisting of nitrogen, argon, neon, helium, methane, ethane, hydrogen, carbon dioxide and mixtures thereof.

Other objects, embodiments, advantages and features of the present invention will be evident to someone of ordinary skill in the chemical engineering art from a detailed examination of the following description of the invention as well as the attached drawings.

TERMS AND CONDITIONS DEFINITIONS

Figure 1:
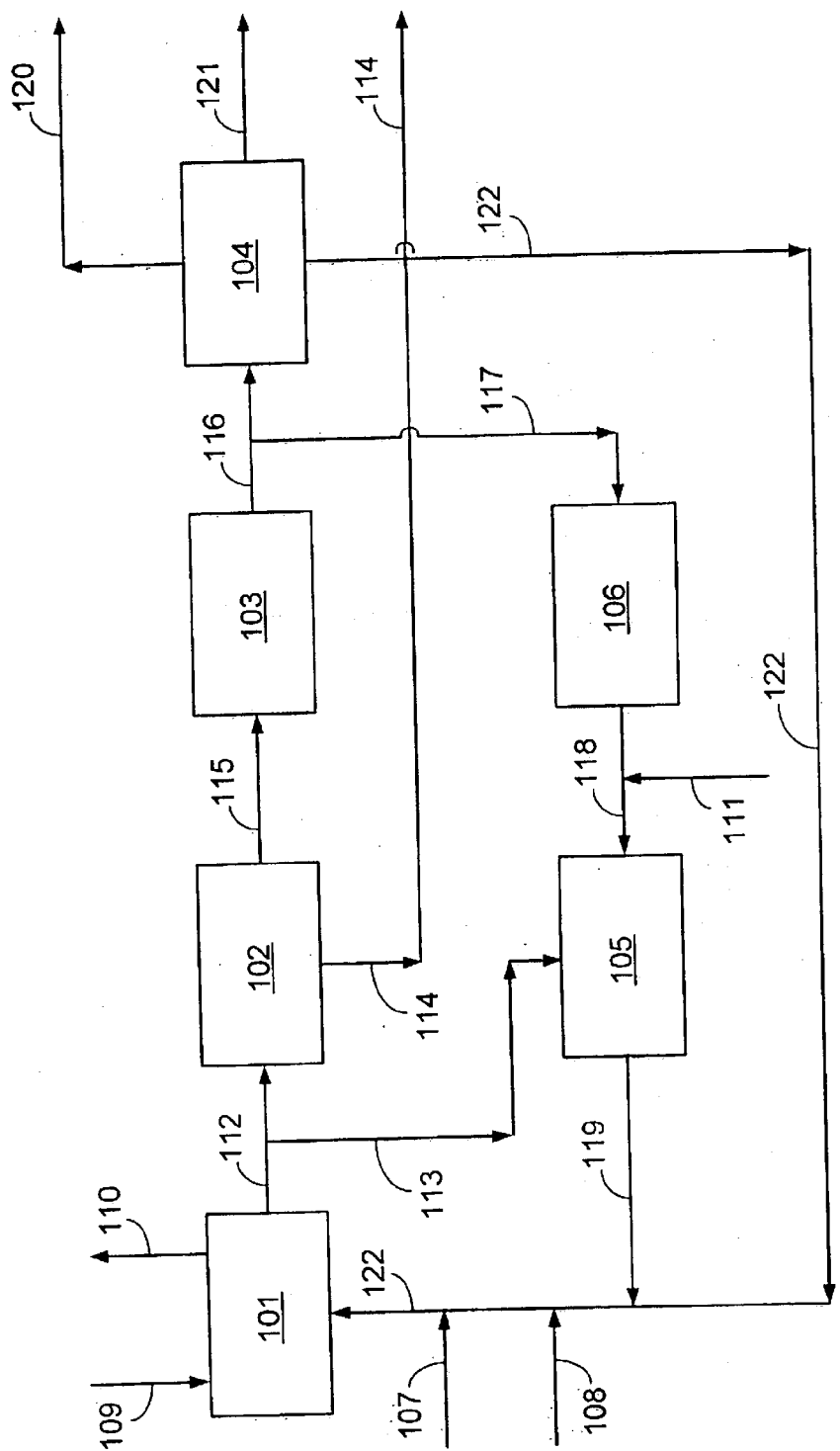
FIG. 1 is a process flow diagram of a preferred embodiment of the present invention which portrays the essential inter-connections and inter-relationships between the operating zones associated with the instant start-up method.

The following terms and conditions are used in the present specification with the following-meanings: (1) a "portion" of a stream means either an aliquot part that has the same composition as the whole stream or a part that is obtained by eliminating a readily separable component therefrom (e.g. if the stream contains hydrocarbons in admixture with steam, then after condensation of a major portion of the steam, it comprises an aqueous portion and a hydrocarbon portion). (2) an "overhead" stream means the net overhead recovered from the specified zone after recycle of any portion to the zone for reflux or any other reason. (3) a "bottom" stream means the net bottom stream from the specified zone obtained after recycle of any portion for purposes of reheating and/or reboiling and/or after any phase separation. (4) a line is "blocked-off" when it contains a valve that is set to a position that prevents flow through the line. (5) presence of necessary compressors and/or pumps is understood when flow is shown from a zone of relatively low pressure to a zone of higher pressure. (6) presence of necessary heating and/or cooling means is implied when flow is shown between zones operating at different temperatures. (7) an ingredient is "lifted" or "stripped" when it is concentrated in the overhead stream withdrawn from the specified zone. (8) a "vapor" stream means a stream containing one or more components in the gaseous state. (9) the term "light olefins" means ethylene, propylene-and mixtures thereof. (10) The expressions "thermal compressor" or "thermal compression zone" means a zone in which one or more ejectors are coupled together in a fashion such that a high pressure motive gas discharges through one or more nozzles at high velocity across a suction chamber which is connected to a suction gas inlet and the resulting discharge gas stream is carried into a venturi-shaped diffuser which converts the velocity energy of the high pressure motive gas into pressure energy which compresses the suction gas and produces a discharge gas stream having a pressure higher then the pressure of the suction gas. These ejectors may be coupled together in multiple stages in serial and/or parallel configurations in order to achieve the desired discharge pressure and since each ejector contains no moving parts it is relatively inexpensive and maintenance free. For additional information on thermal compressors including preferred configuration for multiple ejector designs, see Perry, John H. *Chemical Engineer's Handbook*, $4_{th}$ Ed (New York: McGraw-Hill, 1963), p. 6–29 to 6–31 (all of the teachings of which are specifically incorporated herein by reference). (11) The expression "dry start-up gas" means start-up gas that contains less then 100 vol. ppm $H_2O$, preferably less then 50 vol. ppm more preferably less then 20 vol. ppm $H_2O$. (12) The expression "motor-driven compressor" means a compressor that is driven by a machine for converting various forms of energy into mechanical force and motion such as an electric motor, an internal combustion engine, a steam turbine, a gas turbine and the like engines.

DETAILED DESCRIPTION OF THE INVENTION

The present invention will be described specifically in an MTO embodiment where it is has been established to have great utility thereby allowing someone of ordinary skill in the art to make the necessary modifications for its application in the broader embodiments mentioned above by substitution of the well-known specifics of other included areas of application. In other words, a specific example is used here to enable practice of the instant start-up method in other applications mentioned hereinbefore.

The starting point for the present invention in an MTO embodiment is a MTO conversion step which utilizes methanol as the principal source of the oxygenate reactant. As explained hereinbefore, there are essentially two different approaches to the catalytic conversion of methanol to light olefins. The principal distinction between these two approaches is based on the type of molecular sieve which is used as the active ingredient in the MTO catalyst system and I prefer the non-zeolitic route to MTO conversion. The details associated with this non-zeolitic route to MTO conversion are summarized in U.S. Pat. No. 5,095,163, U.S. Pat. No. 5,126,308 and U.S. Pat. No. 5,191,141, all of the teachings of which are all specifically incorporated herein by reference. As indicated in these teachings, the preferred molecular sieve is a silicoaluminophosphate system, which has been established as occurring in numerous specific crystal structures; As is indicated in the cited patents, the most preferred SAPO structure for MTO conversion has been identified as a SAPO-34 structure. Although the start-up method of the present invention will work equally well with effluent streams from MTO conversion zones that contain zeolitic or non-zeolitic catalyst systems, it is preferred that the effluent stream be derived from an MTO conversion zone that is run with a SAPO-34 catalyst system. The SAPO-34 molecular sieve maybe used alone or may be mixed with a binder and/or filler and formed into shapes such as extrudates, pills, spheres, and the like. Any of the inorganic oxide well known in the art maybe used as a binder and/or filler such as alumina, silica, alumina-phosphate, silica-alumina, and/or one of the various silica-rich clays that are well known to those of ordinary skill in the art. When a binder and/or filler is used in formulating the SAPO-34 catalyst system, SAPO-34 will usually be present in an amount of about 5 to 90 mass-% of the finished catalyst and preferably about 5 to 40 mass-% thereof. It is to be understood that the active ingredient is the SAPO-34 molecular sieve and the binder and/or filler is an inert material that is used to provide structural integrity to the catalyst particles. A SAPO-34 catalyst system is ordinarily used in an MTO embodiment in a particle size suitable for a fluidized reactor system—typically an average particle size of 65 to 85 microns. Best practice with respect to reactor configuration is a fluidized bed catalyst system with a fast-fluidized reactor system being particularly preferred. A good example of the preferred fast-fluidized reactor system is shown in U.S. Pat. No. 6,166,282 the drawing of which is reproduced in this specification as the attached FIG. 2.

The fluidized MTO reaction zone is operated at conditions, which include a temperature of about 300° to 600° C. (572° to 112° F.) with the preferred range being about 450° to 550° C. (842° to 1022° F.). The pressure used in the MTO conversion step is typically in the range of about 138 to 1000 kPa (20 to 145 psi) and preferably from about 170 to 345 kPa (24.7 to 50 psi). The contact time of the reactants with the catalyst is ordinarily measured in terms of a Weight Hourly Space Velocity (WHSV) calculated on the basis of a mass hourly flow rate of the sum of the mass of the methanol reactant passed to the MTO conversion zone, any other oxygenate reactants present in the feed or recycle and any hydrocarbon materials present therein divided by the mass of the SAPO-34 molecular sieve present in the MTO conversion zone. WHSV for use in the MTO conversion zone associated with the present invention can range from 1 to about 100 $hr^{-1}$, with the best results obtained in the range of about 5 to 20 $hr^{-1}$. Since the MTO conversion reaction is strongly exothermic, a significant temperature increase will occur across the reaction zone ordinarily of the magnitude of about 250° to 500° C. (482° to 932° F.). In a fluidized reactor system, a catalyst circulation rate between the reactor and the regenerator will be set at a minimum level desired to hold average coke on the circulating inventory of the preferred SAPO catalyst in a range of about 1 to 20 mass-% of the active ingredient in the catalyst and, more preferably, in the range of about 5 to 17 mass-%.

The regeneration step associated with the MTO conversion step will ordinarily use one of the established oxidative techniques for removing the necessary amount of coke from the catalyst prior to recirculation to the conversion zone. The primary factor that will establish the circulation rate between the conversion zone and the regeneration zone is the equilibrium value of coke on catalyst that it is desired to maintain in order to obtain the desired conversion level. SAPO-34 based catalyst system runs quite successfully at conversion levels of 95% or higher and results in a coke make of approximately 2 to 5 mass-% of methanol equivalents charged to the MTO conversion step. Knowing the coking rate, someone of ordinary skill in the art can then establish a circulation rate to the regenerator based on burning coke at a rate which holds the overall average coke level on the circulating catalyst system used in the MTO conversion zone in the desired range specified hereinbefore. In comparison with traditional FCC operation, the circulation rate for an MTO fluidized conversion zone will be quite low since the regenerated catalyst is not needed to supply heat to the MTO reaction zone.

The methanol feedstock that is charged to the MTO conversion step can ordinarily be used with a diluent as is taught in the prior art acknowledged and incorporated above; however, best practice is not to use a diluent other than autogenously produced steam. The use of a diluent is beneficial in the sense of controlling the partial pressure of the methanol reactant but is disadvantageous in the sense of increasing the volume of the reaction zone and providing additional material that has to be separated from the products in the recovery section of the process. When a diluent is present in the MTO conversion step, it is preferably steam that is derived from the water that is an evitable contaminant of the methanol feed stream as well as of the recycle oxygenate streams. Since in many cases it is desired to charge a crude methanol feed stream containing up to about 20 wt-% water, there may in fact be substantial diluent that is brought into the system with the feed stream. In most cases however, it is preferred to run with a methanol feed stream that is 95 to 99.9 mass-% methanol. It is to be recognized that a substantial amounts of a steam diluent will be autogenously generated in the MTO conversion zone due to the fact that methanol can be calculated to contain over 56 mass-% bound water and due to the fact that the kinetics of the reaction occurring in the MTO reaction zone are such that the initial formation of DME is extremely fast and results in the formation of one mol of a steam diluent for every 2 mols of methanol that react to produce DME.

The effluent stream withdrawn from an MTO conversion zone will therefore contain substantial amounts a water by-product as well as unreacted methanol, substantial quantities of DME intermediate, ethylene, propylene, $C_4$ to $C_6$ olefins and minor amounts of other hydrocarbons and oxygenates. Typically, with the preferred SAPO-34 catalyst system when it is run at 97+ conversion levels, approximately 70 to 78% of the methanol equivalent carbon entering the conversion step will be converted to the desired $C_2$ and $C_3$ olefins with 2 to 5% of the carbon converted to coke and approximately 0.5 to 1% converted to DME. The level of saturated hydrocarbons produced in the MTO conversion step such as methane, ethane and propane are characteristically held at very low levels with a SAPO-34 catalyst and will approximately be 2 to 5% of the carbon balance. The effluent stream exiting the MTO reactor will typically be at a relatively high temperature of 350° to 600° C. (662° to 1112° F.) and must be substantially cooled prior to entering a phase separation zone. Typically, this cooling is done either by heat exchange against the feed methanol stream or by the use of an aqueous quench stream in one or more quenching towers or a combination of both of these techniques. Regardless of the heat exchange technique that is used, it is preferred to substantially cool and, condense at least a substantial portion of the steam by-product contained in the effluent from the conversion zone utilizing a quench zone containing one or more quench towers operated with a cool quenching medium consisting essentially of water and at quenching conditions whereby the effluent stream is partially condensed with recovery of a substantial portion of the water by-product of the MTO conversion zone. The quench zone usually operates at a pressure which is approximately 40 to 95% of the pressure maintained in the MTO conversion zone and the overhead recovered from this quench zone will still contain substantial amounts of water vapor along with the hydrocarbon and oxygenate products of the synthesis reaction. A preferred two-stage quench tower design for this operation is shown in my recently issued patent, U.S. Pat. No. 6,403,854.

It is preferred to take this overhead stream from the quench zone and run it through a product compression zone containing a series of suction drums and variable speed centrifugal compressors in order to elevate its pressure to a range of about 2000 kPa (290 psi) to 2600 kPa (377 psi). The centrifugal compressor typically have relatively flat performances curves which sharply limit their ability to compress volumes of gas beyond their design range. By changing the speed of operation, it is possible to increase their capacity somewhat but this option is usually limited to about 10 to 20% of their rated capacity. Spill-back lines can be used to drop their capacity at a specified outlet pressure and thereby prevent unstable operation giving rise to "surge" conditions. In an MTO embodiment, the compression zone is ordinarily designed to handle only about 20 to 60% of the volume of the effluent gas stream withdrawn from the MTO reaction zone because 40 to 80% of this volume is typically steam, present because of the use of a water diluent in some cases and because water is a substantial by-product of the MTO reaction as previously explained. Best practice here is to size the product compression zone to handle only about 30 to 40% of the volume of the effluent stream withdrawn from the MTO reactor zone during on-stream operations.

The start-up gas used to initiate operations in an MTO process unit as described above can be any gas stream that is inert under the conditions utilized during start-up of the MTO reactor system containing any high performance MTO catalyst particles. It also must be readily available in the quantity required to establish gas circulation in the MTO reactor system and it must not condense in the micropores of any MTO catalyst system that is present in the MTO reactor zone during the start-up procedure. Since the initial start-up temperature of the MTO reactor system can range from ambient (i.e. about −18° to 38° C.) (0° to 100° F.) for a "cold" start-up up to about 300° to 500° C. (572° to 932° F.) during a "hot" start-up which follows an emergency shutdown, it is important that the start-up gas not have a dew point that could cause condensation in the micropores of the MTO catalyst system. Due to capillary attraction forces that may be induced in the smaller micropores of the MTO catalyst system, the micropore dew point for a particular gas may be much higher then that would be measured for the bulk phase using standard dew point measuring techniques. Capillary condensation in the small micropores of the MTO catalyst system is to be avoided since it can unleash undesired stresses in the catalyst particles leading to shattering of some portion of these particles and to wetting of the surface of these particles with resulting formation of what those of skill in fluidization art refer to as "catalyst mud." Formation of catalyst mud is not desired since it can under the right circumstances inhibit catalyst circulation in the fluidized MTO reactor system. It follows from this that in the case of desiring to use a start-up gas containing steam it is important that the steam not be used until the temperature of the catalyst is safely above the micropore dew point for steam which in the case of the preferred SAPO-34 catalyst means a temperature of at least about 300° to 400° C. (572° to 752° F.). Once the MTO reactor system and any catalyst particles contained therein reaches a temperature within or above this safe range, then steam can be safely used as a portion of the start-up gas stream. In some cases, it may be desirable to use a two-step procedure wherein a dry start-up gas stream is utilized to achieve this safe range above the micropore dew point and thereafter high-pressure steam is used to supplement or augment the original start-up gas stream. Given these limitations, it is preferred to use a start-up gas selected from the group of nitrogen, hydrogen, carbon dioxide, an inert gas such as argon, helium or neon and a light saturated hydrocarbon such as methane or ethane. Mixtures of these gases can also be used if such a mixture is conveniently available. The preferred start-up gas is a dry nitrogen until the catalyst and the MTO unit reaches a temperature safely above the micropore dew point temperature after which a mixture of steam and nitrogen can be safely used as explained above.

Figure 2:
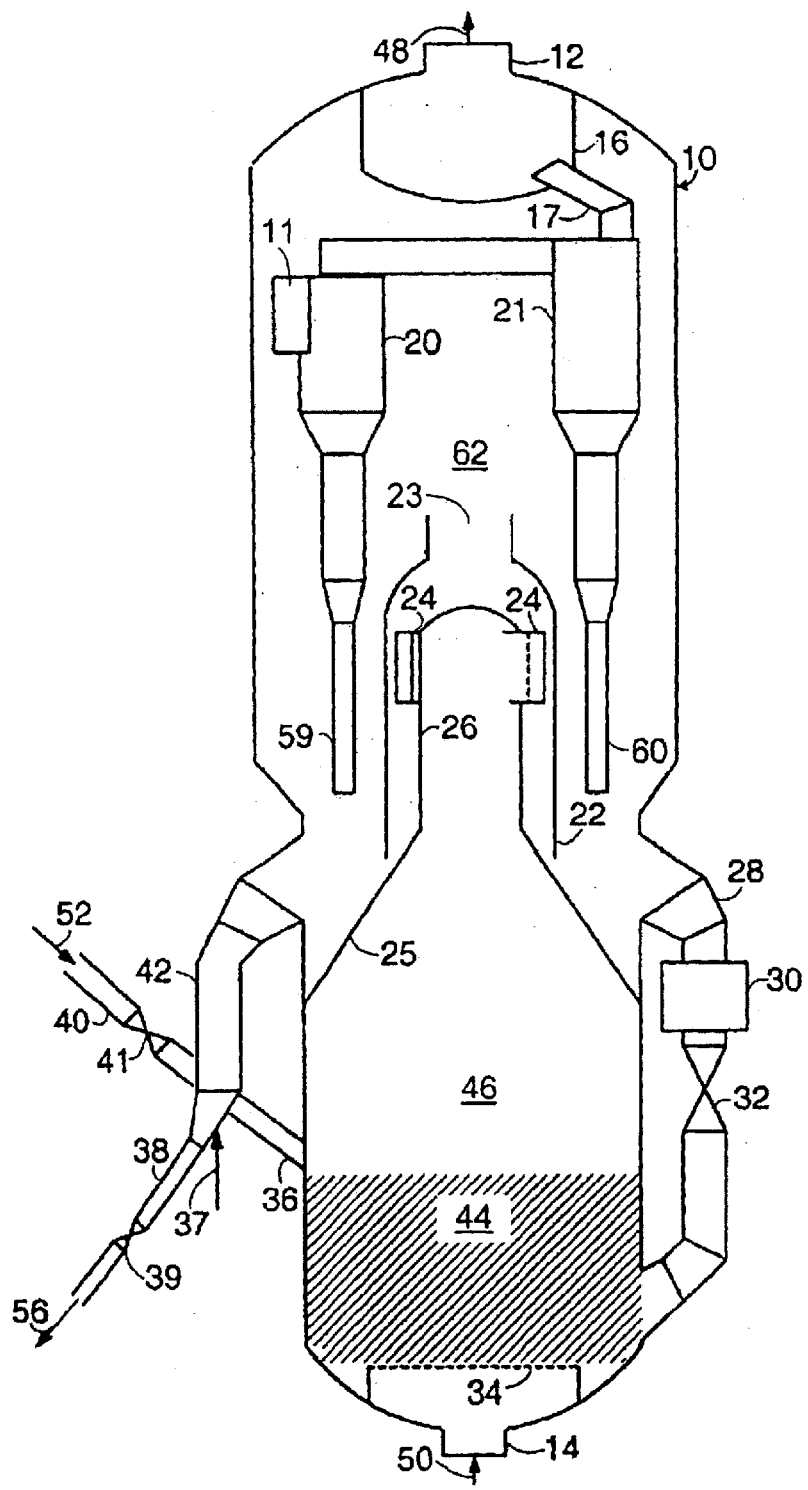
FIG. 2 is a schematic diagram of a preferred fast-fluidized bed reactor system for use in an MTO process that is started up by means of the present invention.

For the preferred fast-fluidized reactor configuration shown in FIG. 2, MTO reactor zone hydraulics are ordinarily set so that good catalyst fluidization and circulation are obtained in a commercial scale unit with a target pressure differential across the reactor zone.(i.e. from gas inlet to product gas outlet) of about 48 to 103 kPa (7 to 15 psi). Higher pressure differentials are not ordinarily beneficial because of the risk of overloading the cyclones which are designated in FIG. 2 as items 20 and 21 and thereby causing detrimental amounts of the expensive MTO catalyst system to be blown out of the top of the reactor in the product gas stream 48. When the target pressure differential is achieved both during start-up and onstream operations, then there is sufficient driving force across the reactor to achieve the critical superficial linear velocity of the gas stream being circulated through the reactor system to achieve proper and effective operation of cyclones 20 and 21 and thereby effectively separating the expensive MTO catalyst system from the product gas stream and retaining it in the disengagement zone of the MTO reactor system where it can be effectively recycled back to the dense phase reaction zone. The critical superficial linear velocity that must be achieved for proper operation of the cyclones is measured at the inlet throat to the first stage cyclone and corresponds to about 10.7 to 16.8 m/sec (35 to 55 ft/sec) and even more preferably from about 12.2 to 15.2 m/sec (40–50 ft/sec). In a nut shell then, successful start-up of a commercial scale fast-fluidized MTO reactor system requires sufficient compressor capacity to achieve target pressure differential across the reactor at an effluent flow rate of about 60 to 70%, or more of the on-stream design effluent flow rate measured in terms of volume per second. Once this condition is established, then the critical superficial linear velocity limitation specified above is achieved and catalyst circulation can safely commence.

A schematic outline of the inter-relationships and interconnections between the various zones that are involved in the instant MTO process start-up method is presented in the attached FIG. 1. Zone 101 is the MTO reaction zone which is shown having a catalyst inlet 109 and a catalyst outlet 110 which are used to charge the reaction zone initially with the MTO catalyst and during onstream operations are used to circulate spent catalyst from the reaction zone to an oxidative regeneration zone (not shown) via line 110 where catalyst is regenerated and returned to zone 101 via line 109. Start-up gas is charged to zone 101 via line 107 and 122 in order to provide the initial charge of start-up gas which is then circulated through two different recycle circuits having a common last leg which comprises lines 119 and 122 as will be explained below. Methanol feed stream enters zone 101 via lines 108 and 122 in order to commence MTO conversion operations at the appropriate point in the start-up procedure. An effluent gas stream is shown as being withdrawn from zone 101 via line 112. During the initial portion of the start-up protocol this gas stream is essentially the circulating start-up gas stream. Once feed is introduced, then it becomes a mixture of MTO reaction products and start-up gas during a transition period from the initiation of the MTO reaction until the unit is fully onstream at which point the effluent gas withdrawn via line 112 will be entirely MTO reaction products. At the intersection of line 112 with line 113, the effluent gas stream from MTO reaction zone 101 is divided into two streams. Because as previously explained the product compressor zone associated with a commercial MTO reaction zone is only designed to handle about 20 to 60% of the volume of the effluent gas stream withdrawn via line 112 at the onstream design capacity for the particular unit. The split that occurs at the junction of line 113 with 112 will be such that about 40 to 60% of the volume of the start-up gas effluent stream flows through line 112 directly into zone 102 and the remaining portion will pass via line 113 into zone 105. For convenience, the split of the effluent gas stream that occurs during start-up at this junction is characterized as being into two separate start-up gas circuits. The first portion of the start-up gas effluent stream that goes to zone 102 is the high-pressure circuit whereas the second portion that goes through line 113 to thermal compression zone 105 is the low-pressure circuit. Zone 102 is the quench zone which as was previously explained is designed to condense the significant amount of water vapor that during onstream operations is present in the MTO reaction zone effluent. During start-up, this zone 102 need not function until MTO conversion operations are commenced. Since there is very little pressure drop associated with passing a gas stream through zone 102 when the quenching medium is not being circulated, the first portion of the effluent gas is shown as being passed there through. In some cases, it may be convenient to bypass zone 102 until the point in the start-up protocol where feed is introduced and pass this first portion directly to product compression zone 103 via means not shown. In the attached drawing, quench zone 102 is shown as producing two outlet streams. The first of these is an overhead stream withdrawn via line 115 and during onstream operations comprises the hydrocarbon portion of the effluent stream that is withdrawn from the MTO conversion zone. During the start-up procedure, it will transport the first portion of the start-up effluent gas stream to zone 103. The second output stream from zone 102 is the water by-product stream which during on-stream operation is withdrawn therefrom via line 114. Since during start-up the aqueous quenching medium need not be circulated in zone 102 until the introduction of methanol feed stream commences, line 114 will be blocked-off until that point in the start-up protocol. It is to be noted that zone 102 preferably has one or more quench tower with quenching medium recirculation loops around each of them, which are not shown in the attached drawing. Quench zone 102 can be operated in one or more stages and a particularly preferred two stage operation is shown in UOP's patent, U.S. Pat. No. 6,403,854.

After traversing zone 102, the first portion of start-up gas is passed via line 115 into product compression zone 103 which contains one or more high speed centrifugal compressors along with there associated suction drums and heat exchangers which are designed to increase the pressure of the hydrocarbon portion of the MTO reaction zone effluent from a range of about 90 to 897 kPa (13 to 127 psi) in order to produce a high pressure start-up gas stream having a pressure of about 2000 to 2600 kPa (290 to 377 psi). During start-up in accordance with the present invention, the product compressor train is used to raise the pressure of the first portion of the effluent gas stream to the indicated range in order to produce high pressure gas stream 116 which is shown in the drawing as flowing to the intersection of line 116 with line 117. There is a valve in line 116, not shown, which is downstream of this junction and during the initial portion of the instant start-up method before feed introduction is used to block off the portion of line 116 that leads to product recovery zone 104.

Product recovery zone 104 is the light olefin and oxygenate recovery zone which during the onstream portion of the MTO process is utilized to recover a light olefin product stream which is withdrawn therefrom via line 120, a heavy olefin product stream which is withdrawn therefrom via line 121 and an oxygenate recycle stream which is withdrawn therefrom via line 122. This oxygenate recycle stream essentially comprises DME and methanol which is recycled via line 122 to MTO reaction zone 101 during the onstream portion of the MTO process. During the first stage of the start-up protocol before feed is charged to zone 101, zone 104 is blocked off and it only comes into the picture during the second stage of the start-up routine when the methanol feed stream is slowly introduced into the process via lines 108 and 122 after catalyst circulation is safely established in zone 101.

Returning to the high pressure start-up gas stream from zone 103, at least a first portion is withdrawn from product compression zone 103 via lines 116 and 117 and passed to start-up heating zone 106 in which the high pressure gas stream is heated to a temperature which is preferably at least about 300° to 400° C. (572° to 752° F.) or more in order to provide a heated and compressed start-up gas stream which is passed via line 118 to the motive gas inlet of thermal compression zone 105. Also shown in the drawing as being charged to zone 105 is high pressure steam which enters the system via line 111 and flows via line 118 to the motive gas inlet of thermal compression zone 105. In accordance with the teaching hereinbefore given with respect to avoidance of mud formation in MTO reaction zone 101, line 111 is blocked off until the MTO reaction zone 101 and any catalyst contained therein reach a temperature safely above the micropore dew point as specified herein before.

Thermal compression zone 105 contains one or more ejectors that are connected in serial and/or parallel configurations in order to enable a heated and compressed gas stream to compress a low pressure gas stream to produce a discharge gas stream which has a pressure intermediate the high pressure stream and the low pressure stream. In the particular case illustrated in FIG. 1, the heated and compressed first portion of the start-up effluent gas that flows through line 118 is the motive gas for the thermal compressor and it passes through one or more nozzles contained in the thermal compressor into a suction chamber which is connected to the second portion of effluent gas stream (i.e. low pressure gas stream) passing directly to zone 105 via lines 112 and 113. Line 113 will contain a check valve (not shown) which will only permit flow towards zone 105. The thermal compression is utilized to produce a compressed gas stream 119 (i.e. the discharge gas stream) which is of intermediate pressure between the low-pressure gas stream in line 113 and the high-pressure gas stream in line 118. The low-pressure gas stream is ordinarily referred to in the thermal compression art as the "suction gas." Zone 105 is described as having only one stage of compression but of course it is intended to cover a multiple stage option wherein the ejectors are serially inter-connected so that the discharge gas from the first stage is used as the motive gas for the second stage etc.

Thermal compression zone 105 acts to produce a discharge gas stream which is about 3–10 times the pressure of the low pressure gas which passes there to through line 113 and more preferably is about 4 to 7 times the pressure of the low pressure gas stream. This discharge gas stream is then charged to MTO reaction zone 101 via lines 119 and 122 thereby completing both start-up gas recycle circuits. A pressure differential across MTO reaction zone 101 is then created by means of the undersized (i.e. for start-up purposes) product compression zone 103 and the use of thermal compression zone 105. This flow scheme obviates the need for a dedicated start-up compressor of a size significantly greater then the product compression zone in order to circulate the start-up gas stream.

The heated intermediate pressure start-up gas stream (i.e. the discharge gas stream) that is discharged from thermal compressions 105 via line 119 flows via line 122 back to MTO reaction zone 101 where it is used to heat this zone as well as any catalyst contained therein until a temperature of about 300° to 400° C. (572° to 752° F.) is reached in zone 101. As the start-up gas stream is recirculated through the two recycle circuits that are described above and heated by means of the start-up heater in zone 106, the pressure of the start-up gas stream (i.e. the discharge gas stream) circulated through lines 119 and lines 122 increases until it builds to the point where the pressure differential across MTO reaction zone 101 is sufficient to drive the start-up gas stream there through at the superficial linear gas velocity required for effective gas separation in the cyclones that are associated with fluidized MTO reaction zone 101.

A particularly preferred fast-fluidized reactor system is shown in the attached FIG. 2 wherein the fast-fluidized bed reactor operates to produce light olefins from oxygenates such as methanol utilizing a SAPO-34 type of fluidized catalyst system. This preferred fast-fluidized bed reactor 10 comprises a disengaging zone 62 and a lower reaction zone consisting of a dense phase zone 44 and a transition phase zone 46. During on-stream operation, a methanol-containing feedstock which may contain other oxygenates selected from the group consisting of ethanol, dimethylether, and the like is passed via line 50 to the feed inlet 14 in the presence of any optional diluent. The feedstock and optional diluent admixture passes through a feed distributor 34 and enters the dense phase zone 44. The feed distributor 34 consists of a uniformly flat sieve plate which permits the vapor phase feed admixture to pass through while retaining a catalyst above the sieve plate. Generally, the feed distributor 34 is supported by a ring having an overall diameter smaller than the outside diameter of the generally circular feed distributor. A plurality of legs is disposed on the base of the reactor to support the ring. The legs are typically welded to the ring at right angles to the sieve plate to form a feed distributor assembly and the feed distributor assembly is rigidly disposed on the base of the lower reaction zone above the feed inlet 14. The ring serves to support the catalyst bed and to reduce vibrations in the feed distributor 34. As the feedstock enters the dense phase zone 44, the feedstock contacts the non-zeolitic small pore catalyst typically containing SAPO-34, and reacts at effective conditions to produce a reaction product gas stream. The reaction product gas stream comprises steam, olefins, including ethylene, propylene, butylene and other hydrocarbons. In the course of the reaction, a carbonaceous deposit is produced on the catalyst particles, reducing the activity of the catalyst. The reaction product gas stream and a catalyst particle mixture comprising active catalyst and some deactivated catalyst are conveyed into the transition phase zone 46 in an intermediate portion of the reaction zone. As the reaction product and the catalyst mixture continue moving upwardly through the lower reaction zone into a riser section 26, the cross-sectional area of the flow path-through the fast-fluidized bed reactor is reduced from the cross-sectional area of the dense phase zone 44 by a reducing means 25, or cone section, to the cross-sectional area of the riser section 26. In the fast-fluidized bed reaction system, the superficial gas velocity through the transition phase zone 46 varies between about 1 to 3 m/sec (about 3 to 10 ft/sec). The riser section 26 has as smaller diameter and a smaller cross-sectional area than the dense phase zone 44 which increases the superficial gas velocity through the riser relative to the dense phase zone 44. Because the superficial gas velocities in the riser section 26 are higher for the same feed rate, the cross-sectional area of the overall reactor zone can be decreased by about a factor of 2 or 3 times compared to the cross-sectional area of a bubbling bed reactor. In addition, the fast-fluidized bed reaction zone provides more precise control of the feedstock and catalyst rates without the need for external catalyst addition or removal. As a result,.the fast-fluidized bed reaction system provides significantly decreased catalyst inventories over a bubbling bed reactor. The riser section discharges the reaction product stream and catalyst mixture through a separation zone consisting of distributor arms 24, or discharge opening, and a separation vessel 22. The discharge opening 24 tangentially discharges the reaction product stream and catalyst mixture to create a centripetal acceleration of the catalyst and gas within the separation vessel 22 that provides an initial stage cyclonic separation. The catalyst mixture falls to the bottom of the disengaging zone 62 which defines a particle outlet for discharging fluidized catalyst particles and the vapor portion of the reaction product stream passes upwardly through a gas recovery outlet 23 for withdrawing gaseous fluids from the separation vessel 22. The vapor, comprising entrained catalyst particles, continues upwards to a dilute phase separator typically in the form of a series of one to three conventional cyclone separation stages shown in the drawing as 20 and 21. Cyclone separation stage 20 having a vapor/solid inlet 11 represents a primary cyclone separation wherein a primary cyclone vapor stream is passed to a secondary cyclone separation stage 21 and the secondary vapors from the secondary cyclone separation stage 21 are conveyed via conduit 17 to a plenum chamber 16; A net reaction product effluent stream comprising less than about 100 ppm-%wt catalyst particle is withdrawn via line 48 from the reactor outlet 12. Preferably, the net reaction product effluent stream withdrawn from the fast-fluidized bed reaction zone comprises less than about 70 ppm-wt catalyst. Catalyst separated in the primary cyclone separation stage 20 drops through dip leg 59 into the bottom of the disengaging zone 62. Catalyst separated from the reaction product in the secondary cyclone separation stage falls through dip leg 60 into the bottom of the disengaging zone 62. Dip legs 59 and 60 are fitted with flapper valves (not shown) at their base to prevent the back flow of vapors through the cyclone separators Catalyst accumulated in the bottom of the disengaging zone 62 is allowed to achieve an upper catalyst level and any excess catalyst is passed through at least one external catalyst recirculation standpipe 28 through a recirculation slide valve 32, and returned to the dense phase zone 44. Preferably, at least two external catalyst recirculation standpipes are employed to return catalyst from the disengaging zone 62 to the dense phase zone 44. Optionally, a heat transfer zone 30, such as a conventional flow-through catalyst cooler, is disposed in at least one external catalyst recirculation standpipe at a point above the recirculation slide valve 32. The use of the catalyst cooler allows the recovery and removal of excess heat from the exothermic reactions taking place in the reaction zone. Heat is typically removed from the catalyst to produce steam, which can be used elsewhere in the complex. As the reaction proceeds, the activity of the catalyst in the reaction zone gradually is reduced by the buildup of coke on the catalyst. To maintain the conversion and selectivity of the reaction at acceptable levels, a portion of the catalyst mixture is withdrawn as a spent catalyst stream from the upper disengaging zone 62 and passed through a spent catalyst standpipe 42. In the spent catalyst standpipe 42, the spent catalyst stream is stripped with a stripping medium such as steam introduced via line 37 to produce a stripped catalyst stream 56. The spent catalyst standpipe 42 will typically include a stripping section that contains grids or baffles to improve contact between the catalyst and the stripping medium. The stripped catalyst stream is conveyed through line 38 and the spent catalyst slide valve 39. The stripped catalyst stream 56 is passed to a catalyst regeneration zone (not shown). In the catalyst regeneration zone, the spent catalyst stream is at least partially regenerated either by oxidation of coke to produce a regenerated catalyst stream. A regenerated catalyst stream 52 is returned to the lower reaction zone via a regenerated catalyst standpipe comprising line 40, regenerated catalyst slide valve 41, and line 36 to a point above the dense phase zone 44. The regenerated catalyst return is shown at a point above the dense phase zone. The return of the regenerated catalyst to the reaction zone may be provided at any point in the riser or in the upper catalyst bed. Preferably, the dense phase zone is operated to maintain a bed height of between about 2 meters (7 feet) and about 6 meters (20 feet) above the feed distributor 34 and below the intermediate portion of the reaction zone in the dense phase zone. More preferably, the bed height of the dense phase zone comprises between about 2.4 meters (8 feet) and about 4 meters (13 feet). By maintaining this bed height in the dense phase zone 44, feedstock flow variations and "jet penetration" at the feed distributor are minimized to provide a well-mixed reaction zone. Returning the regenerated catalyst to the point above the dense phase zone 44 improves the selectivity of the overall reaction toward ethylene and propylene.

In the case of the start-up of fast-fluidized bed reactor zone 10, it is necessary to consider two broad cases. The first is a "cold" start-up in which the inventory of fluidized particles of catalyst can be either located in the disengagement zone 62 with the slide valve 32 located in recirculation line 28 blocked off or the catalyst inventory in zone has not yet been established and must be loaded into the reactor via catalyst return leg 52 as part of the start-up protocol. The other case to consider is of course due to an emergency shutdown typically caused by a power failure in one or more of the pumps and/or compressors that-drive: the feed inlet or product recovery sections of the overall MTO process. In this hot shut down case, an inventory of hot catalyst will be present in fast-fluidized reactor 10 in disengagement zone 62 with both the catalyst withdrawal leg 42 and the catalyst recirculation leg 28 being blocked off via slide valves 39 and 32. In either case, it is necessary to utilize the two recycle start-up gas circuits described in conjunction with FIG. 1 to establish a flow of a heated start-up gas stream through fast-fluidized reactor 10 from inlet 50 to gas outlet 48 until the hereinbefore specified temperature of reaction zone 10 is achieved and the pressure differential across reactor 10 establishes a circulating start-up gas flow velocity which meets the previously specified critical superficial gas velocity requirement for operation of cyclones 20 and 21. Once both the pressure differential and a temperature safely above the micropore dew point temperature of the catalyst are achieved via the recirculating heated start-up gas stream, then catalyst circulation can be started by opening slide valve 32 provided the necessary inventory of catalyst required is present in disengagement zone 62. If however the catalyst inventory has to be established as part of the start-up routine, then once the circulating start-up gas reaches the specified temperature and pressure differential, a catalyst inventory can be charged into dense phase zone 44 via catalyst return leg 52 with slide valve 41 being open and once the necessary inventory in disengagement zone 62 accumulates the slide valve 32 can be opened to start catalyst recirculation. In the case of a "hot" start-up, the inventory of catalyst in reactor 10 as well as the hardware associated therewith will already be at a temperature that is substantially above the micropore dew point of the catalyst and thus the circulation of the start-up gas through the two recycle circuits previously described in conjunction with FIG. 1 will be considerably shortened and the start-up gas will be recirculated until the pressure differential across zone. 10 is sufficient to meet the critical superficial gas velocity requirements of cyclones 20 and 21. In either case, the start-up protocol requires the initiation of catalyst circulation via opening of slide valve 32 and allowing the recirculating start-up gas stream entering reaction 10 via line 50 to transport the catalyst from dense phase zone 44 through transition phase zone 46 into disengagement zone 62 wherein substantially all of the catalyst is separated from the circulating start-up gas and returned through recycle dip leg 28 with slide valve 32 being open. During this period, the effluent gas stream withdrawn from reactor 10 via line 48 is checked to make sure that the cyclones are functioning properly. Once this is established, then injection of a minor amount of methanol feed stream via lines 107 and 122 in FIG. 1 (corresponds to inlet line 50 in FIG. 2) is commenced.

After good catalyst circulation is established in the reaction zone with the recirculation of start-up gas (i.e. discharge gas from thermal compression zone 105 in FIG. 1), the next step is a transition step-wherein the recirculating start-up gas is gradually replaced by vaporized methanol feed which is FIG. 1 enter reactor zone 101 via lines 108 and 122. During the transition period, the fluidizing gas in reaction zone I 01 will be a mixture of methanol feed and discharge gas from thermal compression zone 105. When feed injection starts, quenching zone 102 is also started-up by circulating the quenching medium into contact with the effluent gas stream withdrawn from reactor zone 101 and charged to quench zone 102 as was previously explained. The resulting cooled and quenched portion of effluent gas stream withdrawn from quench zone 102 via line 115 flows into compression zone 103 wherein its pressure is substantially elevated. At the junction of line 116 with line 117, the resulting compressed effluent gas stream is divided into two portions. The first portion flowing via line 117 to start-up heating zone 106 and into the first start-up gas current. During this transition step however, the valve (not shown) blocking entry of the second portion of the high pressure gas stream into light olefins and oxygenate recovery zone 104 is gradually opened and product recovery operation in zone 104 are brought on line. During the transition step, the amount of the second portion of the high pressure gas stream charged to product recovery zone 104 is gradually increased at a rate directly commensurate with the rate of increase of the amount of methanol feed charged to reaction zone 101. As the amount of this second portion of high pressure gas stream 116 is increased, the amount of the first portion directed to start-up heating zone 106 via lines 111 and 117 will proportionately drop until the first start-up gas current is effectively blocked-off and all of the cooled and quenched effluent gas stream hows from zone 103 is passed directly to product recovery zone 104.

The rate at which methanol feed replaces recirculated start-up gas in this transition step depends on a number of factors including the size of this unit, how long it takes to line-out at a particular feed level, the activation energy associated with the desired MTO reaction, the coking rate of the catalyst system used, and various other factors well known to those of ordinary skill-in the art. A preferred transition sequence involves an initial introduction of feed in an increment of about 5 to about 15% of the design capacity of the unit and then a gradual increase in the level of feed in similar sized increments as the unit responds to each increment and lines-out at the resulting intermediate feed flow rate. Once this transition step is completed, the unit will be up and running in its designed on-stream operating mode as previously described and zones 105 and 106 will be blocked off and shutdown.

In sum then, the invention provides a substantial capital savings in that the purchase of a dedicated and expensive motor-driven compressor for use exclusively in the start-up of the process unit is obviated.

I claim as my invention:

1. A method of starting up a catalytic process comprising a fluidized reactor zone containing one or more cyclones requiring a minimum superficial gas velocity in order to function properly and a motor-driven product compression zone that is sized to handle only about 20 to 60 vol-% of the reaction zone effluent gas stream at design capacity and that cannot during start-up provide the required superficial gas velocity for the one or more cyclones where the start-up is conducted without the use of an additional motor-driven start up compressor and with the use of a thermal compressor having a motive gas inlet, where the process is an MTO process and that feed contains methanol a suction gas inlet, and a discharge gas outlet, the start-up-method comprising the steps of:

a) charging the reaction zone with an inert start-up gas in an amount sufficient to provide an effluent gas stream for recirculation;

b) passing a first portion of the resulting effluent gas stream to the product compression zone and compressing it therein to provide a high pressure gas stream;

c) heating at least a first portion of the high pressure gas stream, charging the resulting heated high pressure gas stream to the motive gas inlet of the thermal compressor to produce a discharge gas stream and recycling the resulting discharge gas stream from the thermal compressor back to the reaction zone thereby establishing a first start-up gas circuit;

d) passing a second portion of the effluent gas stream from step a) directly to the suction gas inlet of the thermal compressor, compressing the second portion using energy contained in the motive gas and passing the resulting compressed gas into the discharge gas stream thereby establishing a second start-up gas circuit;

e) increasing the temperature of the heated high pressured gas stream until the temperature of the reaction zone reaches at least about 300° to 400° C. (572° to 752° F.);

f) increasing the pressure of the discharge gas stream until the pressure differential across the reaction zone is sufficient to drive the discharge gas stream there through at a velocity which meets or exceeds the minimum cyclone superficial gas velocity;

g) start circulating catalyst particles in the reactor zone using the discharge gas stream from the thermal compressor as the fluidizing gas and charging a minor amount of feed to the reaction zone while passing a commensurate second portion of the high pressure gas stream produced in step b) to a product recovery zone; and h) increasing the amount of feed passed to the reaction zone while simultaneously decreasing the amount of the first portion of the high pressure gas stream passed into the first start-up gas circuit until the desired flow rate of the feed into the reaction zone is established and the-thermal compressor is blocked off.

2. The start-up method as defined in claim 1 wherein the inert start-up gas is selected from the group consisting of nitrogen, hydrogen, carbon dioxide, argon, neon, helium, methane, ethane and mixtures thereof.

3. The start-up method as defined in claim 1 wherein high pressure steam is injected into the motive gas inlet of the thermal compressor in admixture with the heated high pressure gas stream once the temperature of the MTO reaction zone reaches a level of about 300° to 400° C. (572° to 752° F.).

4. The start-up method as defined in claim 1 wherein the fluidized reaction zone is a fast-fluidized reaction zone containing a dense phase catalyst reactor section and a catalyst disengagement section that contains an inventory of catalyst particles and wherein catalyst circulation is initiated in step g) by opening a slide valve in a catalyst recirculation standpipe providing a conduit between the disengagement section and the dense phase reactor-section.

5. The start-up method as defined in claim 1 wherein step g) is performed with a fluidized reaction zone that does not initially contain catalyst, where the fluidized reaction zone comprises a dense phase reactor section and a catalyst disengagement section and where step g) is performed in two sub-steps:
   a) adding catalyst to the fluidized reaction zone via a catalyst inlet standpipe which is in communication with the dense phase reactor section until the required inventory of catalyst accumulates in the disengagement zone; and
   b) opening a slide valve in a recirculation standpipe providing a flow conduit between the disengagement zone and the dense phase reaction zone.

6. The start-up method as defined in claim 1 wherein the fluidized conversions zone is a fast-fluidized reactor.

7. The start-up method as defined in claim 6 where the superficial velocity required for effective separation of the catalyst in the one or more cyclones is about 10.7 to 16.8 m/sec(35 to 55 ft/sec).

8. The start-up method as defined in claim 1 where the product compression zone is designed to handle only about 30 to 40% of the volume of the effluent gas stream exiting the fluidized reactor at design capacity.

9. The start-up method as defined in claim 1 where the catalyst comprises SAPO-34.

10. A method of starting up a catalytic MTO process comprising a fluidized MTO reactor zone containing one or more cyclones requiring a minimum superficial gas velocity in order to function properly, an effluent quench zone, a motor-driven product compression zone that is sized to handle only about 20 to 60 vol-% of the MTO reaction zone effluent gas stream at design capacity and that cannot provide the required superficial linear velocity for the fluidized MTO reaction zone and a light olefin and oxygenate recovery zone, where the start-up is-conducted without the use of an additional motor-driven start-up compressor and with the use of a thermal compressor having a motive gas inlet, a suction gas inlet, and a discharge gas outlet, the start-up method comprising the steps of:
   a) charging the MTO reaction zone with an inert start-up gas in an amount sufficient to provide effluent gas stream for recirculation;
   b) passing a first portion of the resulting effluent gas stream to the product compression zone and compressing it therein to provide a high pressure gas stream;
   c) heating at least a first portion of the high pressure gas stream, charging the resulting heated high pressure gas stream to the motive gas inlet of the thermal compressor to produce a discharge gas stream and recycling the resulting discharge gas stream from the thermal compressor back to the MTO reaction zone thereby establishing a first start-up gas circuit;
   d) passing a second portion of the effluent gas stream from step a) directly to the suction gas inlet of the thermal compressor, compressing the second portion using energy contained in the motive gas and passing the resulting compressed gas into the discharge gas stream thereby establishing a second start-up gas circuit;
   e) increasing the temperature of the heated high pressured gas stream until the temperature of the MTO reaction zone reaches at least about 300° to 400° C. (572° to 752° F.);
   f) increasing the pressure of the discharge gas stream until the pressure differential across the MTO reaction zone is sufficient to drive the discharge gas stream there through at a velocity which meets or exceeds the minimum cyclone superficial gas velocity;
   g) start circulating catalyst particles in the MTO reactor zone using the discharge gas stream from the thermal compressor as the fluidizing gas and charging a minor amount of the methanol feed to the MTO reaction zone while contacting a quenching medium in the quench zone with the effluent gas stream in order to condense stream contained therein and while-passing a commensurate second portion of the high pressure gas stream produced in step b) into the light olefin and oxygenate recovery zone; and
   h) increasing the amount of the methanol feed charged to the MTO reaction zone while simultaneously decreasing the amount of the first portion of the high pressure gas stream passed into the first start-up gas circuit until the desired flow rate of the methanol feed into the MTO reaction zone is established and the thermal compressor is blocked off.

11. The start-up method as defined in claim 10 wherein the inert start-up gas is selected from the group consisting of nitrogen, hydrogen, carbon dioxide, argon, neon, helium, methane, ethane and mixtures thereof.

12. The start-up method as defined in claim 10 wherein a high pressure steam is injected into the motive gas inlet of the thermal compressor in admixture with the heated high pressure gas stream once the temperature of the MTO reaction zone reaches a level of about 300° to 40°° C. (572° to 752° F.).

13. The start-up method as defined in claim 10 wherein the active ingredient of the fluidized catalyst comprises SAPO-34.

14. The start-up method as defined in claim 13 wherein the catalyst comprises SAPO-34 in admixture with an inert binder and/or filler in an amount sufficient to comprise about 5 to 40 mass-% thereof.

15. The start-up method is defined in claim 10 wherein the fluidized MTO reaction zone is a fast-fluidized reaction zone containing a dense phase catalyst reactor section and a catalyst disengagement section that contains an inventory of catalyst particles and wherein catalyst circulation is initiated in step g) by opening a slide valve in a catalyst recirculation standpipe providing a conduit between the disengagement section and the dense phase reactor section.

16. The start-up method as defined in claim 10 wherein step g) is performed with a fluidized MTO reaction zone that does not initially contain catalyst, where the fluidized MTO reaction zone comprises a dense phase reactor section and a catalyst disengagement section and wherein step g) is performed in two sub-steps:
   a) adding catalyst to the fluidized reaction zone via a catalyst inlet standpipe which is in communication with the dense phase reactor section until the required inventory of catalyst accumulates in the disengagement zone; and
   b) opening a slide valve in a recirculation standpipe providing a flow conduit between the disengagement zone and the dense phase reaction zone.

17. The start-up method as defined in claim 10 wherein the fluidized MTO conversion zone is a fast-fluidized reactor.

18. The start-up method as defined in claim 17 where the superficial velocity required for effective separation of the catalyst in the one or more cyclones is about 10.7 to 16.8 m/sec(35 to 55 ft/sec).

19. The start-up method as defined in claim 17 where the product compression zone is designed to handle only about 30 to 40% of the volume of the effluent gas stream exiting the fast-fluidized reactor at design capacity.

* * * * *

UNITED STATES PATENT AND TRADEMARK OFFICE
CERTIFICATE OF CORRECTION

PATENT NO. : 6,872,867 B1
DATED : March 29, 2005
INVENTOR(S) : John J. Senetar

It is certified that error appears in the above-identified patent and that said Letters Patent is hereby corrected as shown below:

Column 20,
Lines 12-13, after "gas inlet," delete "where the process in an MTO process and that feed contains methanol".
Line 14, after "gas outlet," insert -- where the process is an MTO process and the feed contains methanol --.

Signed and Sealed this

Thirty-first Day of May, 2005

JON W. DUDAS
*Director of the United States Patent and Trademark Office*